(12) United States Patent
Lewis

(10) Patent No.: US 7,585,991 B2
(45) Date of Patent: Sep. 8, 2009

(54) (PENTAFLUOROPHENYL) GROUP 11 AND 12 METAL COMPOUNDS, PROCESSES FOR PREPARING (PENTAFLUOROPHENYL) GROUP 11 AND 12 METAL COMPOUNDS, AND USES THEREOF

(76) Inventor: Stewart P. Lewis, 400 Fairfax Rd., N111, Blacksburg, VA (US) 24060

( * ) Notice: Subject to any disclaimer, the term of this patent is extended or adjusted under 35 U.S.C. 154(b) by 0 days.

(21) Appl. No.: 12/009,297

(22) Filed: Jan. 17, 2008

(65) Prior Publication Data

US 2008/0177015 A1    Jul. 24, 2008

Related U.S. Application Data

(60) Provisional application No. 60/885,485, filed on Jan. 18, 2007.

(51) Int. Cl.
*C07F 5/00*    (2006.01)
*C07F 9/00*    (2006.01)
*C07F 3/00*    (2006.01)
*C07F 15/00*   (2006.01)
*C07C 211/00*  (2006.01)

(52) U.S. Cl. .............. 556/1; 556/70; 556/121; 556/144; 564/305; 568/3; 568/17

(58) Field of Classification Search .............. 556/1, 556/70, 121, 144; 564/305; 568/3, 17
See application file for complete search history.

(56) References Cited

U.S. PATENT DOCUMENTS

| 5,427,991 A | * | 6/1995 | Turner ............... 502/103 |
| 5,744,646 A | | 4/1998 | Wilson et al. |
| 7,196,149 B2 | | 3/2007 | Collins et al. |

OTHER PUBLICATIONS

Gusev et al., Organometallics, vol. 25, No. 11, pp. 2750-2760 (published on the Web Apr. 20, 2006).*

* cited by examiner

*Primary Examiner*—Porfirio Nazario Gonzalez
(74) *Attorney, Agent, or Firm*—Renner, Kenner, Greive, Bobak, Taylor & Weber

(57) ABSTRACT

(Pentafluorophenyl) Group 11 and 12 metal compounds and processes for preparing (pentafluorophenyl) Group 11 and 12 metal compounds are disclosed. Also, disclosed are processes for preparing (pentafluorophenyl) Group 13 or 15 metal compounds useful as Lewis acids. Compositions with low levels of base impurities and products produced by the novel processes are also disclosed.

17 Claims, No Drawings

(PENTAFLUOROPHENYL) GROUP 11 AND 12 METAL COMPOUNDS, PROCESSES FOR PREPARING (PENTAFLUOROPHENYL) GROUP 11 AND 12 METAL COMPOUNDS, AND USES THEREOF

CROSS-REFERENCE TO RELATED APPLICATIONS

This application claims the benefit of U.S. Provisional Patent Application No. 60/885,485, filed Jan. 18, 2007, which application is incorporated herein by reference.

FIELD OF THE INVENTION

The present invention relates to processes for preparing (pentafluorophenyl) Group 11 and 12 metal compounds and their use in improved processes for preparing (pentafluorophenyl) Group 13 and 15 metal compounds useful as Lewis acids.

BACKGROUND OF THE INVENTION (Pentafluorophenyl) Group 13 and 15 metal compounds are strong Lewis acids and have many useful industrial applications. In particular, they are useful as catalyst activators in combination with metallocene catalysts in Ziegler-Natta polymerizations and as co-initiators in combination with proton sources and/or carbocation synthetic equivalents for cationic polymerizations.

Despite the utility of (pentafluorophenyl) Group 13 and 15 metal compounds little improvement has been made in their manufacture. Three main strategies have been used for the synthesis of these compounds each possessing drawbacks. One strategy involves the preparation of a pentafluorophenylmagnesiumhalide (Grignard reagent) in an ethereal solvent followed by reaction with a Group 13 or 15 metal halide. These reactions are inefficient in terms of yield. The Grignard reagent is thermally unstable in the absence of an ethereal solvent, has a limited shelf life, and requires special handling. The ethereal solvent also forms a complex with the product and its removal is energy intensive and in some cases it is impossible to remove. Another methodology involves substitution of pentafluorophenyllithium ($C_6F_5Li$) for the Grignard reagent in the displacement reaction with the Group 13 or 15 metal halide. This results in improved product yields. Pentafluorophenyllithium is very thermally unstable and in order to avoid explosion it must be prepared and reacted at low temperatures. Reaction is also typically conducted in the presence of an ethereal solvent that must be removed from the end product. Even though yields are improved this method suffers from energy and safety considerations. A third approach for the synthesis of (pentafluorophenyl) Group 13 and 15 metal compounds is transmetallation. This involves reaction of a precursor pentafluorophenyl metal compound (typically mercury, cadmium, or tin) with a Group 13 or 15 metal halide. In some cases yields are good but the precursor pentafluorophenyl metal compounds are toxic. In certain cases coordinating solvents are required for reaction and their complete removal can be difficult. Synthesis of the precursor pentafluorophenyl metal compound itself may require the use of a pentafluorophenyllithium or Grignard reagent. In such a case transmetallation offers no distinct benefit compared to direct reaction of a pentafluorophenyllithium or pentafluorophenylmagnesiumhalide reagent with a Group 13 or 15 metal halide.

Tris(pentafluorophenyl)boron $\{B(C_6F_5)_3\}$ was first prepared by Massey and Park via reaction of pentafluorophenyllithium and boron trichloride ($BCl_3$) in pentane at $-78°$ C. Not only is this chemistry inherently dangerous to conduct but yields are relatively low and were reported to range from 30-50%. Due to the thermal instability of pentafluorophenyllithium subsequent investigators used pentafluorophenylmagnesium-bromide ($BrMgC_6F_5$) in conjunction with the diethyl etherate complex of boron trifluoride $\{BF_3.O(CH_2CH_3)_2\}$ for the preparation of $B(C_6F_5)_3$. This procedure gives rise to improved yields (c.a., 80%). Although safer from an operational standpoint, removal of the ethereal solvents used in this method requires additional steps such as azeotropic distillation or sublimation and is energy intensive and time consuming.

Following the discovery of $B(C_6F_5)_3$, several (pentafluorophenyl) Group 15 compounds were prepared, including tris(pentafluorophenyl)phosphine $\{P(C_6F_5)_3\}$ and tris(pentafluorophenyl)phosphine oxide $\{OP(C_6F_5)_3\}$. $P(C_6F_5)_3$ was prepared in 39.5% yield by reaction of phosphorus trichloride ($PCl_3$) with $BrMgC_6F_5$ in ether. This method suffers from low yields. $OP(C_6F_5)_3$ was prepared in 97.1% yield by oxidation of $P(C_6F_5)_3$ with sodium dichromate ($Na_2Cr_2O_7$) in a mixture of sulfuric and acetic acids. Later, both tris(pentafluorophenyl)arsenic $\{As(C_6F_5)_3\}$ and tris(pentafluorophenyl)antimony $\{Sb(C_6F_5)_3\}$ in addition to $P(C_6F_5)_3$ were prepared. This was accomplished by reaction of $C_6F_5MgBr$ with $AsCl_3$, $SbCl_3$, and $PSCl_3$ in diethyl ether respectively. This method suffers from low product yields $\{25\%$ for $P(C_6F_5)_3$, 39% for $As(C_6F_5)_3$, and 32% for $Sb(C_6F_5)_3\}$. Subsequent researchers substituted pentafluorophenyllithium in place of the Grignard reagent for the preparation of these compounds. This resulted in improved product yields $\{85\%$ for $P(C_6F_5)_3$, 75% for $As(C_6F_5)_3$, and 75% for $Sb(C_6F_5)_3\}$. Due to the thermal instability of the lithium reagent however, these reactions had to be conducted at $-78°$ C. unfortunately. The synthesis of tris(pentafluorophenyl)amine $\{N(C_6F_5)_3\}$ proved to be more difficult than the other aforementioned (pentafluorophenyl) Group 15 compounds. Other researchers were able to prepare $N(C_6F_5)_3$ by reaction of $HN(C_6F_5)_2$ with hexafluorobenzene in the presence of the strong base p-tolylsodium. Reaction was conducted at $230°$ C. for 42 hours to afford $N(C_6F_5)_3$ in 24% yield. This procedure suffers from drastic reaction conditions and low yields.

Preparation of the diethyl etherate adduct of tris(pentafluorophenyl)gallium $\{Ga(C_6F_5)_3.O(CH_2CH_3)_2\}$ from reaction of gallium trichloride ($GaCl_3$) and $BrMgC_6F_5$ in diethyl ether is known. Although this procedure gives rise to $Ga(C_6F_5)_3.O(CH_2CH_3)_2$ in 65% yield, researchers were unable to remove the coordinated diethyl ether. The synthesis of base free $Ga(C_6F_5)_3$ was not possible until much later. The first disclosure of a method for making base free $Ga(C_6F_5)_3$ involved the reaction of elemental iodine with $Ga(C_6F_5)_3.O(CH_2CH_3)_2$ to form uncomplexed $Ga(C_6F_5)_3$ and an iodine-diethyl ether adduct, the latter being removed by distillation under reduced pressure. The yield of uncomplexed $Ga(C_6F_5)_3$ as produced by this method has not been disclosed. This method suffers from the use of environmentally unfriendly iodine. A second method for the preparation of uncomplexed $Ga(C_6F_5)_3$ involves the exchange reaction between $B(C_6F_5)_3$ and trimethylgallium $\{Ga(CH_3)_3\}$. This strategy purportedly gives rise to high yields of uncomplexed $Ga(C_6F_5)_3$ but involves the requisite use of expensive and pyrophoric $Ga(CH_3)_3$ in addition to consuming valuable $B(C_6F_5)_3$.

Synthesis of the diethyl etherate complex of tris(pentafluorophenyl)indium $\{In(C_6F_5)_3.Et_2O\}$ is also known. This involved the reaction of $BrMgC_6F_5$ with indium trichloride in diethyl ether to give In($C_6F_5$)$_3$.Et$_2$O in 34% yield. No method for removing the complexed diethyl ether was provided. This method suffers from low yields and the inability to form uncomplexed In($C_6F_5$)$_3$. Uncomplexed In($C_6F_5$)$_3$ was first prepared by researchers, who developed three different strategies for manufacture of this compound. The first involved direction reaction of neat IC$_6F_5$ with excess In metal. In($C_6F_5$)$_3$ was isolated in a low yield of 31% via sublimation from the reaction mixture. The second method involved reaction of pentafluorophenylmagnesiumchloride with indium trichloride in tetrahydrofuran (THF) followed by treatment of the crude product with dioxane/ether to yield the complex In($C_6F_5$)$_3$.dioxane in 41% yield. Despite the increased yield no means of obtaining uncomplexed In($C_6F_5$)$_3$ was described. A third procedure involved transmetallation of In metal with Hg($C_6F_5$)$_2$. This resultant product mixture was contaminated with metallic mercury and purification required fractional sublimation to ultimately afford In($C_6F_5$)$_3$ in 53% yield. This method suffers from the toxicity of the precursor mercury compound.

Synthesis of the diethyl ether adduct of tris(pentafluorophenyl)aluminum {Al($C_6F_5$)$_3$.O(CH$_2$CH$_3$)$_2$} from reaction of aluminum trichloride (AlCl$_3$) and pentafluorophenylmagnesiumbromide (BrMgC$_6F_5$) in diethyl ether is also known. However, attempts at removing the coordinated ether resulted in explosion. The synthesis of base free Al($C_6F_5$)$_3$ was not possible until much later. The first disclosure of a method for making base free Al($C_6F_5$)$_3$ was provided by researchers in 1995. This was accomplished by reaction of Me$_2$AlCl with $C_6F_5$Li in hexanes to initially form Me$_2$AlC$_6F_5$ which is then heated to 180° C. in vacuo to liberate AlMe$_3$ and generate crude Al($C_6F_5$)$_3$. Recrystallization of the crude reaction product from THF gave the adduct THF.Al($C_6F_5$)$_3$ in 64% yield. This procedure is dangerous to conduct as $C_6F_5$Li is thermally unstable and the produced Al($C_6F_5$)$_3$ is energetic and exploded on occasion. An alternative route for the synthesis of Al($C_6F_5$)$_3$ involves the exchange reaction between B($C_6F_5$)$_3$ and trimethylaluminum which is typically conducted in an aromatic hydrocarbon (i.e., toluene). This strategy purportedly gives rise to high yields of base free Al($C_6F_5$)$_3$ (stable in toluene) but involves the requisite use of pyrophoric Al(CH$_3$)$_3$ in addition to consuming valuable B($C_6F_5$)$_3$.

The synthesis of Bi($C_6F_5$)$_3$ by certain methods known. Some researchers prepared this compound from the reaction of $C_6F_5$MgBr with bismuth trichloride (BiCl$_3$) in diethyl ether. Yields of Bi($C_6F_5$)$_3$ obtained from this method were low (c.a., 30%). Other researchers prepared Bi($C_6F_5$)$_3$ via transmetallation of bismuth tribromide (BiBr$_3$) with Cd($C_6F_5$)$_2$.diglyme in acetonitrile. Although this procedure improved product yields (71%), it suffers from the use of toxic cadmium compounds. Isolation of uncoordinated Bi($C_6F_5$)$_3$ from this method also requires distillation of diglyme from the product under reduced pressure, a process that is time consuming and energy intensive.

From the foregoing it is clear that there is a need for an improved process for preparing uncomplexed (pentafluorophenyl) Group 13 and 15 metal compounds in a highly efficient manner with improved industrial applicability. Ideally, such a process would be safe to operate and have reduced impact on the environment. The present invention is directed to these, as well as other, important needs.

It is previously known in the art that Group 11 and 12 pentafluorobenzoates can be decarboxylated to yield the corresponding (pentafluorophenyl) Group 11 and 12 metal compounds. Several methods for the synthesis of Group 11 and 12 pentafluorobenzoates have been previously disclosed. One method involves neutralization of pentafluorobenzoic acid with a Group 11 or 12 metal oxide, hydroxide, or carbonate under aqueous conditions followed by dehydration of the reaction mixture. Another strategy involves the reaction of pentafluorobenzoic acid with a Group 11 or 12 metal acetate in an organic solvent followed by the removal of volatiles. A final methodology involves contacting a Group 1 or 2 metal salt of pentafluorobenzoic acid with a Group 11 or 12 metal halide under aqueous conditions followed by dehydration of the reaction mixture.

Since (pentafluorophenyl) Group 11 or 12 metal compounds are readily decomposed by protic materials such as water, pentafluorobenzoic acid, and acetic acid, materials that are typically either liberated and/or used in the synthesis of the Group 11 and 12 pentafluorobenzoates by the aforementioned methodologies, it is important to remove all traces of such materials from the produced Group 11 and 12 pentafluorobenzoates prior to decarboxylation to prevent a reduction in yield. From an environmental and cost standpoint it is most desirable to have a method for preparing Group 11 and 12 pentafluorobenzoates free of protic materials that does not require the use of solvents. The present invention is also directed to these, as well as other, important needs.

SUMMARY OF THE INVENTION

Any one or more of the foregoing aspects of the present invention, together with the advantages thereof over the known art relating to processes for preparing (pentafluorophenyl) Group 11 and 12 metal compounds and their use in improved processes for preparing (pentafluorophenyl) Group 13 and 15 metal compounds useful as Lewis acids, which shall become apparent from the specification that follows, may be accomplished by the invention as hereinafter described and claimed.

In one aspect, the invention provides a process comprising the steps of: contacting, in a bulk melt state, (i) pentafluorobenzoic acid with a Group 11 or 12 metal oxide, a Group 11 or 12 metal hydroxide, a Group 11 or 12 metal carbonate, or a Group 11 or 12 metal acetate under neutralizing conditions; or (ii) a Group 1 or 2 metal salt of pentafluorobenzoic acid with a Group 11 or 12 metal halide, to form a Group 11 or 12 pentafluorobenzoate; removing any volatiles; and decarboxylating said Group 11 or 12 pentafluorobenzoate to form a (pentafluorophenyl) Group 11 or 12 metal compound.

In another embodiment of the invention, the invention provides a process further comprising the step of: contacting said (pentafluorophenyl) Group 11 or 12 metal compound with a Group 13 or 15 metal halide to form a (pentafluorophenyl) Group 13 or 15 metal compound.

In yet another embodiment of the invention, the invention provides a composition comprising a (pentafluorophenyl) Group 13 or 15 metal compound; and less than 0.1%, by weight, based on the total weight of the composition, of a base.

In still another embodiment of the invention, the invention provides a compound of the formula:

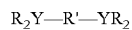

wherein Y is Ga, In, N, P, As, Sb, or Bi; each R is independently selected from the group consisting of a perfluorophenyl; 3,5-bis(trifluoromethyl)phenyl; 1-perfluoronaphthyl; 2-perfluoronaphthyl; 2-perfluorobiphenyl; 3-perfluorobiphenyl; 4-perfluorobiphenyl; and p-($C_1$-$C_{10}$ alkyl)$_3$Si-2,3,5,6-tetra-fluorophenyl; and R' is 1,2-perfluorophenylenyl; 1,2-perfluoronaphthalenyl; 2,3-perfluoronapthalenyl; 1,8-perfluoronaphthalenyl; 1,2-perfluoroanthracenyl; 2,3- perfluoroanthracenyl; 1,9-perfluoroanthracenyl; 1,2-perfluorophenanthrenyl; 2,3-perfluorophenanthrenyl; 1,10-perfluorophenanthrenyl; 9,10-perfluorophenanthrenyl; 2,2'-perfluorobiphenylenyl; 2,2'-perfluoro-1,1'-binaphthalenyl; 3,3'-perfluoro-2,2'-binaphthalenyl; or 1,1'-ferrocenyl.

In yet a further embodiment, the present invention provides a compound of the formula:

wherein Y is B; and each R is independently selected from the group consisting of a perfluorophenyl; 3,5-bis(trifluoromethyl)phenyl; 1-perfluoronaphthyl; 2-perfluoronaphthyl; 2-perfluorobiphenyl; 3-perfluorobiphenyl; 4-perfluorobiphenyl; and p-($C_1$-$C_{10}$ alkyl)$_3$Si-2,3,5,6-tetra-fluorophenyl.

The foregoing general description and the following detailed description are exemplary and explanatory only and are not restrictive of the invention, as defined in the appended claims.

DETAILED DESCRIPTION OF ILLUSTRATIVE EMBODIMENTS

As used herein and in the appended claims, the singular forms "a," "an," and "the" include the plural reference unless the context clearly indicates otherwise. Thus, for example, a reference to "a compound" is a reference to one or more compounds and equivalents thereof known to those skilled in the art, and so forth.

The phrase "bulk melt state," as used herein, refers to a system where all reactants are melted together in the substantial absence (i.e., preferably, less than about 1% by weight, based on the total weight of the composition) of any solvent.

The phrase "base free," as used herein, refers to a composition where there are no electron pair donors (Lewis bases) present.

The phrase "Group 1 metal," as used herein, refers to a metal in Group 1, in accordance with the IUPAC system for numbering elements, and includes lithium (Li), sodium (Na), potassium (K), rubidium (Rb), cesium (Cs), and francium (Fr).

The phrase "Group 2 metal," as used herein, refers to a metal in Group 2, in accordance with the IUPAC system for numbering elements, and includes beryllium (Be), magnesium (Mg), calcium (Ca), strontium (Sr), barium (Ba), and radium (Ra).

The phrase "Group 11 metal," as used herein, refers to a metal in Group 11, in accordance with the IUPAC system for numbering elements, and includes copper (Cu), silver (Ag), gold (Au), and roentgenium (Rg).

The phrase "Group 12 metal," as used herein, refers to a metal in Group 12, in accordance with the IUPAC system for numbering elements, and includes zinc (Zn), cadmium (Cd), mercury (Hg), and ununbium (Uub).

The phrase "Group 13 metal," as used herein, refers to a metal in Group 13, in accordance with the IUPAC system for numbering elements, and includes boron (B), aluminum (Al), gallium (Ga), indium (In), thallium (Tl), and ununtrium (Uut).

The phrase "Group 15 metal," as used herein, refers to a metal in Group 15, in accordance with the IUPAC system for numbering elements, and includes nitrogen (N), phosphorus (P), arsenic (As), antimony (Sb), and bismuth (Bi).

The phrase "(pentafluorophenyl) Group 13 or Group 15 metal compound," as used herein, refers to the mono, bis, tris, tetrakis, pentakis, and hexakis versions of the (pentafluorophenyl) Group 13 or Group 15 metal compound.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods, and examples are illustrative only and not limiting.

As set forth above, one embodiment of the present invention may be directed toward a process for the preparation of a (pentafluorophenyl) Group 11 or 12 metal compound. In the process, pentafluorobenzoic acid is contacted, in bulk melt state, with an oxide, hydroxide carbonate or acetate of a Group 11 or 12 metal under neutralizing conditions, or, in the alternative, a Group 1 or 2 metal salt of pentafluorobenzoic acid is contacted, in a bulk melt state, with a halide of a Group 11 or 12 metal, to form a Group 11 or 12 pentafluorobenzoate. Volatiles are then removed, and the resultant Group 11 or 12 pentafluorobenzoate is then decarboxylated to form a (pentafluorophenyl) Group 11 or 12 metal compound.

In one or more embodiments, the (pentafluorophenyl) Group 11 or 12 metal compound may comprise one of copper (Cu), silver (Ag), zinc (Zn), cadmium (Cd), or mercury (Hg). In another embodiment, the compound may comprise copper (Cu) or zinc (Zn).

In one or more other embodiments, the Group 1 or 2 metal salt of pentafluorobenzoic acid may comprise lithium (Li), sodium (Na), potassium (K), magnesium (Mg), or calcium (Ca).

In certain embodiments, the step of contacting the pentafluorobenzoic acid or Group 1 or 2 metal salt of pentafluorobenzoic acid with a particularly functionalized Group 11 or 12 metal may be conducted in the substantial absence (i.e., less than about 1%, by weight, based on the total weight of the composition) of solvent or diluent. In certain other embodiments of the process, this step of contacting is effected at a temperature of at least about 100° C.

In certain embodiments, the step of removing volatiles may be carried out at a pressure of from about $1 \times 10^{-4}$ Torr to 760 Torr.

In certain embodiments, the step of decarboxylating may be effected via sublimation. In certain other embodiments of the process, the step of decarboxylating may be effected in the presence of diluent, such as a hydrocarbon diluent. In one or more embodiments, the diluent may be a $C_{6-40}$ aliphatic, alicyclic, or aromatic hydrocarbon (such as, for example, octane, decane, dodecane, diethyltoluene, and combinations thereof). In certain embodiments, the step of decarboxylating is effected at a temperature of about 25° C. to about 330° C. In one or more embodiments, the step of decarboxylating may be effected at a pressure from about $1 \times 10^{-5}$ Pa to about $1 \times 10^3$ Pa.

In certain embodiments, the process of the present invention may further include contacting the (pentafluorophenyl) Group 11 or 12 metal compound with a Group 13 or 15 metal halide to form a (pentafluorophenyl) Group 13 or 15 metal compound. Although it is not necessary, the (pentafluorophenyl) Group 11 or 12 metal compound may be isolated before contacting the Group 13 or 15 metal halide.

In certain embodiments, the (pentafluorophenyl) Group 13 or 15 metal compound may include a metal selected from the group consisting of boron (B), aluminum (Al), gallium (Ga), indium (In), nitrogen (N), phosphorus (P), antimony (Sb), and bismuth (Bi).

In certain embodiments, the step of contacting the (pentafluorophenyl) Group 11 or 12 metal compound with the Group 13 or 15 metal halide may be carried out in a bulk melt state. In certain embodiments of the process, the same step may be carried out at a temperature of at least the melting point of the (pentafluorophenyl) Group 11 or 12 metal compound. In certain embodiments, it may suitable to conduct this step of the reaction in a solvent, such as toluene or benzene, to reduce the risk of explosion.

In one or more embodiments, the step of contacting the (pentafluorophenyl) Group 11 or 12 metal compound with the Group 13 or 15 metal halide may be carried out in a diluent. In at least one embodiment, the diluent may be at least one solvent that does not form a complex with Lewis acids, such as, for example, toluene, dichloromethane, dodecane, and combinations thereof. In at least another embodiment of the invention, this step of contacting may be carried out in the same diluent as used in the step of decarboxylating.

In one or more embodiments, the (pentafluorophenyl) Group 11 or 12 metal compound may be any of the following:
bis(pentafluorophenyl)zinc, $Zn(C_6F_5)_2$;
bis(pentafluorophenyl)copper, $Cu(C_6F_5)_2$; or
pentafluorophenylcopper tetramer, $(CuC_6F_5)_4$.
1,2-bis(copper)-3,4,5,6-tetrafluorobenzene, $1,2\text{-}C_6F_4[Cu]_2$.

In one or more embodiments, the (pentafluorophenyl) Group 13 or 15 metal compound may be any of the following:
tris(pentafluorophenyl)boron;
lithium tetrakis(pentafluorophenyl)borate;
sodium tetrakis(pentafluorophenyl)borate;
potassium tetrakis(pentafluorophenyl)borate;
triphenylcarbenium tetrakis(pentafluorophenyl)borate;
tris(pentafluorophenyl)aluminum;
lithium tetrakis(pentafluorophenyl)aluminate;
sodium tetrakis(pentafluorophenyl)aluminate;
potassium tetrakis(pentafluorophenyl)aluminate;
triphenylcarbenium tetrakis(pentafluorophenyl)aluminate;
tris(pentafluorophenyl)gallium;
lithium tetrakis(pentafluorophenyl)gallate;
sodium tetrakis(pentafluorophenyl)gallate;
potassium tetrakis(pentafluorophenyl)gallate;
triphenylcarbenium tetrakis(pentafluorophenyl)gallate;
tris(pentafluorophenyl)indium;
tris(pentafluorophenyl)amine;
tris(pentafluorophenyl)phosphorus;
pentakis(pentafluorophenyl)phosphorus;
lithium hexakis(pentafluorophenyl)phosphate;
sodium hexakis(pentafluorophenyl)phosphate;
potassium hexakis(pentafluorophenyl)phosphate;
triphenylcarbenium hexakis(pentafluorophenyl)phosphate;
tris(pentafluorophenyl)arsenic;
pentakis(pentafluorophenyl)arsenic;
lithium hexakis(pentafluorophenyl)arsenate;
sodium hexakis(pentafluorophenyl)arsenate;
potassium hexakis(pentafluorophenyl)arsenate;
triphenylcarbenium hexakis(pentafluorophenyl)arsenate;
tris(pentafluorophenyl)antimony;
pentakis(pentafluorophenyl)antimony;
lithium hexakis(pentafluorophenyl)antimonate;
sodium hexakis(pentafluorophenyl)antimonate;
potassium hexakis(pentafluorophenyl)antimonate;
triphenylcarbenium hexakis(pentafluorophenyl)antimonate;
tris(pentafluorophenyl)bismuth;
pentakis(pentafluorophenyl)bismuth;
lithium hexakis(pentafluorophenyl)bismate;
sodium hexakis(pentafluorophenyl)bismate;
potassium hexakis(pentafluorophenyl)bismate;
triphenylcarbenium hexakis(pentafluorophenyl)bismate;
1,2-bis[di(perfluorophenyl)gallium]-3,4,5,6-tetrafluorobenzene;
1,2-bis[di(perfluorophenyl)indium]-3,4,5,6-tetrafluorobenzene;
1,2-bis[di(perfluorophenyl)amino]-3,4,5,6-tetrafluorobenzene;
1,2-bis[di(perfluorophenyl)phosphorus]-3,4,5,6-tetrafluorobenzene;
1,2-bis[di(perfluorophenyl)bismuth]-3,4,5,6-tetrafluorobenzene;
1,2-bis[di(perfluorophenyl)arsenic]-3,4,5,6-tetrafluorobenzene; or
1,2-bis[di(perfluorophenyl)antimony]-3,4,5,6-tetrafluorobenzene.

In certain embodiments, the processes of the invention further include the step of recovering the (pentafluorophenyl) Group 13 or 15 metal compound. In some embodiments, the step of recovering may be effected by sublimation of the (pentafluorophenyl) Group 13 or 15 metal compound. In certain other embodiments, the step of recovering may be effected by solubilizing the (pentafluorophenyl) Group 13 or 15 metal compound in at least one solvent that does not form a complex with Lewis acids (such as, for example, toluene, dichloromethane, dodecane, and combinations thereof) to form a solution, filtering or decanting the solution, and, optionally, evaporating the solvent to recover the purified (pentafluorophenyl) Group 13 or 15 metal compound.

In yet other embodiments, the present invention may be directed to compositions comprising a (pentafluorophenyl) Group 13 or 15 metal compound, and less than 0.1%, by weight, based on the total weight of the composition, of a base. In one or more embodiments, the composition may include less than about 0.05%, by weight, based on the total weight of the composition, of a base.

In yet other embodiments, the invention is directed to the products produced by any of the processes described herein.

In further embodiments, the invention is directed to compounds of the formula:

$$R_2Y-R'-YR_2$$

wherein Y is Ga, In, N, P, As, Sb, or Bi; each R is independently selected from the group consisting of a perfluorophenyl; 3,5-bis(trifluoromethyl)phenyl; 1-perfluoronaphthyl; 2-perfluoronaphthyl; 2-perfluorobiphenyl; 3-perfluorobiphenyl; 4-perfluorobiphenyl; and p-$(C_1\text{-}C_{10}$ alkyl$)_3$Si-2,3,5,6-tetra-fluorophenyl; and R' is one of 1,2-perfluorophenylenyl; 1,2-perfluoronaphthalenyl; 2,3-perfluoronapthalenyl; 1,8-perfluoronaphthalenyl; 1,2-perfluoroanthracenyl; 2,3-perfluoroanthracenyl; 1,9-perfluoroanthracenyl; 1,2-perfluorophenanthrenyl; 2,3-perfluorophenanthrenyl; 1,10-perfluorophenanthrenyl; 9,10-perfluorophenanthrenyl; 2,2'-perfluorobiphenylenyl; 2,2'-perfluoro-1,1'-binaphthalenyl; 3,3'-perfluoro-2,2'-binaphthalenyl; or 1,1'-ferrocenyl. These compounds, as well as the other (pentafluorophenyl) Group 13 and 15 compounds set out above, are believed to be useful as catalyst activators in combination with metallocene catalysts in Ziegler-Natta polymerizations (for forming polyethylene, for example) and as co-initiators in combination with proton sources and/or carbocation synthetic equivalents for cationic polymerizations. In certain embodiments of these compounds, the compounds are selected from the group consisting of:

1,2-bis[di(perfluorophenyl)gallium]-3,4,5,6-tetrafluorobenzene;
1,2-bis[di(perfluorophenyl)indium]-3,4,5,6-tetrafluorobenzene;
1,2-bis[di(perfluorophenyl)amino]-3,4,5,6-tetrafluorobenzene;
1,2-bis[di(perfluorophenyl)phosphorus]-3,4,5,6-tetrafluorobenzene;
1,2-bis[di(perfluorophenyl)arsenic]-3,4,5,6-tetrafluorobenzene;
1,2-bis[di(perfluorophenyl)antimony]-3,4,5,6-tetrafluorobenzene; and
1,2-bis[di(perfluorophenyl)bismuth]-3,4,5,6-tetrafluorobenzene.

In further other embodiments, the invention is directed to compounds of the formula:

$$R_2Y-YR_2$$

wherein Y is B; and each R is independently selected from the group consisting of a perfluorophenyl; 3,5-bis(trifluoromethyl)phenyl; 1-perfluoronaphthyl; 2-perfluoronaphthyl; 2-perfluorobiphenyl; 3-perfluorobiphenyl; 4-perfluorobiphenyl; and p-($C_1$-$C_{10}$ alkyl)$_3$Si-2,3,5,6-tetra-fluorophenyl. Notably, the form of chelating diboron compound does not have an organic spacer between the two Lewis acid centers (Boron atoms).

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

Example 1

Preparation of Zinc Pentafluorobenzoate, $Zn(O_2CC_6F_5)_2$

A 1 L single neck round bottom flask was charged with 90.00 g (4.100×10$^{-1}$ mol) zinc (II) acetate dihydrate, 173.80 g (8.2000×10$^{-1}$ mol) pentafluorobenzoic acid, and a magnetic stir bar. The flask was then fitted with a reflux condenser and heated to 150° C. Within 30 minutes from the start of heating a homogeneous melt was obtained. The melt was held at this temperature for an additional hour after which the condenser was replaced with a short path vacuum distillation setup. Volatiles were then removed under reduced pressure and upon completion of distillation of acetic acid and water small amounts of unreacted pentafluorobenzoic acid sublimed out. 198.00 g (4.0610×10$^{-1}$ mol, 99.00% yield) pentafluorobenzoate was obtained as a white solid. $^1$H and $^{19}$F NMR showed this material to be >99% pure. $^{19}$F NMR (acetone-d$_6$, 300K, 376.29 MHz) δ–140.62 (d, 4F, o-$C_6F_5$), –154.38 (t, 2F,p-$C_6F_5$), –163.10 (m, 4F, m-$C_6F_4$).

Example 2

Preparation of Bis(pentafluorophenyl)zinc, $Zn(C_6F_5)_2$

A sublimator was charged with 40.00 g (8.204×10$^2$ mol) zinc pentafluorobenzoate followed by a layer of glass wool and a perforated Pyrex® glass disc. The sublimator was placed under dynamic vacuum and heated to 330° C. for 1 hour during which bis(pentafluorophenyl)zinc collected on the cold finger as it was liberated. The crude material was then recrystallized once from toluene to yield 26.22 g (6.564×10$^{-2}$ mol, 80.00% yield) of bis(pentafluorophenyl)zinc. $^1$H and $^{19}$F NMR showed this material to be >98% pure. $^{19}$F NMR (toluene-d$_8$, 300K, 376.29 MHz) δ–118.06 (d, 4F, o-$C_6F_5$), –152.69 (t, 2F, p-$C_6F_5$), –160.60 (m, 4F, m-$C_6F_4$).

Example 3

Preparation of Bis(pentafluorophenyl)zinc, $Zn(C_6F_5)_2$

To a dry Schlenk flask containing a magnetic stir bar under nitrogen, dry $C_6F_5I$ and diethyl zinc may be added via cannula or syringe in such a manner that the molar ratio of these two reagents is about 2:1 respectively. This mixture may then be cooled to 0° C. and then dry acetonitrile may be added via a cannula or syringe. The Schlenk flask may be fitted with a dry air-free distillation head/receiver setup, and the reaction mixture heated to reflux. Upon reflux of the reaction mixture for 6 hours under nitrogen, the iodoethane may then be distilled out. Dry toluene in an amount sufficient to dissolve the produced bis(pentafluorophenyl)zinc may be added via a cannula or syringe and the acetonitrile may be distilled out. The product may be isolated either by recrystallization or by removal of volatiles under reduced pressure.

Example 4

Preparation of Bis(pentafluorophenyl)zinc, $Zn(C_6F_5)_2$

In a glove box, a determined quantity of zinc-copper couple (2 time molar excess compared to the total number of moles of $C_6F_5I$ and $C_6F_5Br$) may be added to a dry Schlenk flask containing a magnetic stir bar. This may be attached to a Schlenk line and may be placed under nitrogen. The Schlenk flask may be fitted with a reflux condenser. Then, a small quantity (such as, for example, about 10% of the total volume to be used for reaction) of an equimolar mixture of dry $C_6F_5I$ and dry $C_6F_5Br$ may be added via cannula or syringe as a solution in toluene {c.a., 1:1, vol:vol ($C_6F_5I+C_6F_5Br$):toluene}. The reaction mixture may be heated to reflux and held at this temperature until reaction begins to start as evidenced by darkening of the zinc-copper couple. Once the reaction has started, the heat source may be removed and the remainder of the $C_6F_5I/C_6F_5Br$ mixture may continue to be added at such a rate to maintain reflux. The mixture may be cooled to 25° C. and the reflux condenser may be replaced with a Schlenk frit/flask assembly and the reaction mixture may be filtered. The filtrate may be concentrated to a solid by removal of volatiles under reduced pressure. If this process does not succeed, higher heat and pressure may be required.

Example 5

Preparation of Bis(pentafluorophenyl)zinc, $Zn(C_6F_5)_2$

A determined quantity of zinc (II) difluoride may be added to a Schlenk flask along with a magnetic stir bar under nitrogen inside a glove box. The Schlenk flask may be sealed and attached to a Schlenk line and placed under nitrogen. A sufficient quantity (enough to dissolve everything) of a suitable dry solvent (i.e., diethyl ether, acetonitrile, toluene, or a combination thereof) may be added either by cannula or vacuum transfer to the Schlenk flask. Next, $(CH_3)_3SiC_6F_5$ may be injected in a quantity such that the molar ratio of this reagent to zinc (II) difluoride is 2:1. The Schlenk flask may be fitted with a reflux condenser, and the reaction mixture refluxed under nitrogen or static vacuum for 12 hours; then, it may be cooled to room temperature. The filtrate may be concentrated to a solid by removal of volatiles under reduced pressure.

Example 6

Preparation of Bis(pentafluorophenyl)zinc, $Zn(C_6F_5)_2$

Dry $C_6F_5I$ may be added via a cannula or syringe to a carius tube containing a magnetic stir bar and zinc metal under nitrogen in such a manner that the molar ratio of these two reagents is 1:2 respectively. The tube may then be subjected to three freeze/pump/thaw cycles and sealed. The tube may then be heated to about 200° C. or higher if necessary for 6 hours. Dry toluene may be added by cannula or syringe in an amount sufficient to dissolve the produced bis(pentafluorophenyl) zinc. The product may be isolated either by recrystallization or by removal of volatiles under reduced pressure.

Example 7

Preparation of Bis(pentafluorophenyl)copper, $Cu(C_6F_5)_2$

A determined quantity of copper (II) difluoride may be added to a Schlenk flask along with a magnetic stir bar under nitrogen inside a glove box. The Schlenk flask may then be sealed and attached to a Schlenk line and placed under nitrogen. A sufficient quantity (enough to dissolve everything) of a suitable dry solvent (i.e., diethyl ether, acetonitrile, toluene, or a combination thereof) may be added either by cannula or vacuum transfer to the Schlenk flask. Next, $(CH_3)_3SiC_6F_5$ may be injected in a quantity such that the molar ratio of this reagent to copper (II) difluoride is about 2:1. The Schlenk flask may be fitted with a reflux condenser, and the reaction mixture refluxed under nitrogen or static vacuum for about 12 hours. Then the reaction mixture may be cooled to room temperature. The filtrate may be concentrated to a solid by removal of volatiles under reduced pressure.

Example 8

Synthesis of 1,2-Bis(copper)-3,4,5,6-tetrafluorobenzene, 1,2-$[Cu]_2C_6F_4$

A three-necked round bottom reaction flask (containing a magnetic stir bar) may be fitted with an air-free solids addition funnel, a nitrogen inlet, and a septum inlet adapter. The assembly may be placed under nitrogen and a determined quantity of 1,2-dibromotetrafluorobenzene or 1,2-diiodotetrafluorobenzene (dissolved in ether) may be added to the flask via cannula. The air-free solids addition funnel may be charged with anhydrous copper (I) halide (e.g. CuBr) so that the molar ratio of 1,2-dihalotetrafluorobenzene to copper (I) halide is about 1:4, respectively. The reaction flask should be cooled to about −78° C. and then butyllithium in hexanes may be added slowly with stirring so that the final molar ratio of 1,2-dihalotetrafluorobenzene to butyllithium is about 1:2.4. After about 2 hours, the copper (I) halide may be added in slowly while maintaining a reaction temperature of −78° C.

Approximately 2 hours following the addition of the copper (I) halide, the reaction mixture should be slowly warmed to room temperature and the air-free solids addition funnel may be replaced with a Schlenk frit/flask assembly. The reaction mixture may be filtered and the filtrate concentrated to a solid by removal of volatiles under reduced pressure. The crude product may be recrystallized from a suitable dry solvent (e.g. toluene, dichloromethane).

Example 9

Synthesis of Lithium Tetrakis(pentafluorophenyl) borate, $LiB(C_6F_5)_4$

Bis(pentafluorophenyl)zinc and a lithium boron (IV) halide (i.e., lithium tetrabromoborate) may be added to a Schlenk flask along with a magnetic stir bar under nitrogen inside a glove box. The molar ratio of these two reagents may be maintained at a level of 2:1, respectively. The Schlenk flask may be sealed and attached to a Schlenk line, then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser, and the reaction mixture refluxed under nitrogen or static vacuum for 12 hours. It may then be cooled to room temperature. Any zinc (II) dihalide that precipitates may be removed by replacing the condenser with a Schlenk frit/flask assembly and filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof). Other Group 1 metal tetrakis(pentafluorophenyl)borate compounds may be made by substitution of the desired Group 1 metal boron (IV) halide (i.e., sodium tetrafluoroborate).

Example 10

Synthesis of Triphenylcarbenium Tetrakis(pentafluorophenyl)borate, $(C_6H_5)_3CB(C_6F_5)_4$ Bis(pentafluorophenyl)zinc, a Group 1 boron (IV) halide (i.e., lithium or sodium tetrabromoborate), and a triphenylcarbenium halide (i.e., a triphenylcarbenium chloride) may be added to a Schlenk flask along with a magnetic stir bar under nitrogen inside a glove box. The molar ratio of these three reagents should be maintained at a level of 2:1:1, respectively. The Schlenk flask may be sealed and attached to a Schlenk line. Then it may be placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser. The reaction mixture may be refluxed under nitrogen or static vacuum for 12 hours and then cooled to room temperature. Any Group 1 metal halide, or zinc (II) dihalide that precipitates may be removed by replacing the condenser with a Schlenk frit/flask assembly and filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof).

Example 11

Synthesis of Triphenylcarbenium Tetrakis(pentafluorophenyl)borate, $(C_6H_5)_3CB(C_6F_5)_4$ Bis(pentafluorophenyl)zinc and a triphenylcarbenium boron (IV) halide (i.e., triphenylcarbenium tetrabromoborate) may be added to a Schlenk flask along with a magnetic stir bar under nitrogen inside a glove box. The molar ratio of these two reagents should be maintained at a level of 2:1, respectively. The Schlenk flask may be sealed and attached to a Schlenk line, and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser. The reaction mixture may be refluxed under nitrogen or static vacuum for 12 hours and then cooled to room temperature. Any zinc (II) dihalide that precipitates may be removed by replacing the condenser with a Schlenk frit/flask assembly and filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof).

Example 12

Synthesis of Tris(pentafluorophenyl)aluminum, $Al(C_6F_5)_3$

An aluminum (III) halide (i.e., aluminum (III) chloride) and a magnetic stir bar may be added under nitrogen inside a glove box. The Schlenk flask may be sealed and attached to a Schlenk line. It may then be placed under nitrogen. Bis(pentafluorophenyl)zinc may be added as a solution in toluene. The molar ratio of this reagent with respect to the aluminum (III) halide should be 3:2, respectively. Any zinc (II) dihalide that precipitates may be removed by fitting the Schlenk flask with a Schlenk frit/flask assembly and filtering the reaction mixture.

Example 13

Synthesis of Lithium Tetrakis(pentafluorophenyl) aluminate, $LiAl(C_6F_5)_4$

Bis(pentafluorophenyl)zinc and a lithium aluminum (IV) halide (i.e., lithium tetrachloroaluminate) may be added to a Schlenk flask along with a magnetic stir bar under nitrogen inside a glove box. The molar ratio of these two reagents should be maintained at a level of 2:1, respectively. The Schlenk flask may be sealed and attached to a Schlenk line, and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser. The reaction mixture may be refluxed under nitrogen or static vacuum for 12 hours and then cooled to room temperature. Any zinc (II) dihalide that precipitates may be removed by replacing the condenser with a Schlenk frit/flask assembly and filtering the reaction mixture. Other Group 1 metal tetrakis(pentafluorophenyl)aluminate compounds may be made by substitution of the desired Group 1 metal aluminum (IV) halide (i.e., sodium tetrachloroaluminate).

Example 14

Synthesis of Triphenylcarbenium Tetrakis(pentafluorophenyl)aluminate, $(C_6H_5)_3CAl(C_6F_5)_4$ Bis(pentafluorophenyl)zinc, a Group 1 aluminum (IV) halide (i.e., lithium or sodium tetrachloroaluminate), and a triphenylcarbenium halide (i.e., triphenylcarbenium chloride) may be added to a Schlenk flask along with a magnetic stir bar under nitrogen inside a glove box. The molar ratio of these three reagents should be maintained at a level of 2:1:1, respectively. The Schlenk flask may be sealed and attached to a Schlenk line, and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser, and the reaction mixture may be refluxed under nitrogen or static vacuum for 12 hours and then cooled to room temperature. Any Group 1 halide, or zinc (II) dihalide that precipitates may be removed by replacing the condenser with a Schlenk frit/flask assembly and filtering the reaction mixture.

Example 15

Synthesis of Triphenylcarbenium Tetrakis(pentafluorophenyl)aluminate, $(C_6H_5)_3CAl(C_6F_5)_4$ Bis(pentafluorophenyl)zinc and a triphenylcarbenium aluminum (IV) halide (i.e., triphenylcarbenium tetrachloroaluminate) may be added to a Schlenk flask along with a magnetic stir bar under nitrogen inside a glove box. The molar ratio of these two reagents should be maintained at a level of 2:1, respectively. The Schlenk flask may be sealed and attached to a Schlenk line, and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser, and the reaction mixture can be refluxed under nitrogen or static vacuum for 12 hours and then cooled to room temperature. Any zinc (II) dihalide that precipitates can be removed by replacing the condenser with a Schlenk frit/flask assembly and filtering the reaction mixture.

Example 16

Preparation of Tris(pentafluorophenyl)gallium, $Ga(C_6F_5)_3$

Inside a glove box under nitrogen a 2L Schlenk flask was charged with 25.00 g ($1.420 \times 10^{-1}$ mol) gallium trichloride, 85.08 g ($2.130 \times 10^{-1}$ mol) bis(pentafluorophenyl)zinc, and a magnetic stir bar. The flask was fitted with a rubber septum, attached to a Schlenk line, and placed under nitrogen. Next, 1

L of dried toluene was cannulated into the flask and then the septum was replaced with a reflux condenser. The reaction mixture was then heated to reflux for 2 hours during which zinc (II) chloride precipitated. The reaction mixture was then allowed to cool to room temperature and the condenser was replaced with a Schlenk frit/flask assembly. The reaction mixture was filtered and the filtrate was reduced to a white solid via removal of volatiles under reduced pressure. This white solid was then purified by sublimation to give 72.90 g ($1.277 \times 10^{-1}$ mol, 90.00 % yield) tris(pentafluorophenyl)gallium as a white solid. $^1$H and $^{19}$F NMR showed this material to be >99% pure. $^{19}$F NMR (benzene-$d_6$, 300K, 376.29 MHz) δ–123.65 (d, 4F, o-$C_6F_5$), –149.58 (t, 2F,p-$C_6F_5$), –160.00 (m, 4F, m-$C_6F_4$).

Example 17

Synthesis of Lithium Tetrakis(pentafluorophenyl) gallate, LiGa($C_6F_5$)$_4$

Bis(pentafluorophenyl)zinc and a lithium gallium (IV) halide (i.e., lithium tetrachlorogallate) may be added to a Schlenk flask along with a magnetic stir bar under nitrogen inside a glove box. The molar ratio of these two reagents should be maintained at a level of 2:1, respectively. The Schlenk flask may be sealed and attached to a Schlenk line, and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser, and the reaction mixture may be refluxed under nitrogen or static vacuum for 12 hours and then cooled to room temperature. Any zinc (II) dihalide that precipitates may be removed by replacing the condenser with a Schlenk frit/flask assembly and filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof). Other Group 1 metal tetrakis(pentafluorophenyl)gallate compounds may be made by substitution of the desired Group 1 metal gallium (IV) halide (i.e., sodium tetrachlorogallate).

Example 18

Synthesis of Triphenylcarbenium Tetrakis(pentafluorophenyl)gallate, ($C_6H_5$)$_3$CGa($C_6F_5$)$_4$ Bis(pentafluorophenyl)zinc, a Group 1 gallium (IV) halide (i.e., lithium or sodium tetrachlorogallate), and a triphenylcarbenium halide (i.e., triphenylcarbenium chloride) may be added to a Schlenk flask along with a magnetic stir bar under nitrogen inside a glove box. The molar ratio of these three reagents should be maintained at a level of 2:1:1, respectively. The Schlenk flask may be sealed and attached to a Schlenk line, and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser, and the reaction mixture may be refluxed under nitrogen or static vacuum for 12 hours and then cooled to room temperature. Any Group 1 metal halide, or zinc (II) dihalide that precipitates can be removed by replacing the condenser with a Schlenk frit/flask assembly and filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof).

Example 19

Synthesis of Triphenylcarbenium Tetrakis(pentafluorophenyl)gallate, ($C_6H_5$)$_3$CGa($C_6F_5$)$_4$ Bis(pentafluorophenyl)zinc and a triphenylcarbenium gallium (IV) halide (i.e., triphenylcarbenium tetrachlorogallate) may be added to a Schlenk flask along with a magnetic stir bar under nitrogen inside a glove box. The molar ratio of these two reagents should be maintained at a level of 2:1, respectively. The Schlenk flask may be sealed and attached to a Schlenk line, and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser. The reaction mixture may be refluxed under nitrogen or static vacuum for 12 hours and then cooled to room temperature. Any zinc (II) dihalide that precipitates may be removed by replacing the condenser with a Schlenk frit/flask assembly and filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof).

Example 20

Synthesis of Petrakis(pentafluorophenyl)phosphorus, P($C_6F_5$)$_5$

Bis(pentafluorophenyl)zinc and a phosphorus (V) halide {i.e., phosphorus (V) bromide} may be added to a Schlenk flask along with a magnetic stir bar under nitrogen inside a glove box. The molar ratio of these two reagents should be maintained at a level of 5:2, respectively. The Schlenk flask may be sealed and attached to a Schlenk line, and then placed under nitrogen or vacuum. A sufficient quantity (enough to dissolve everything) of a suitable dry solvent (i.e., toluene, dichloromethane, dodecane, or a combination thereof) may be added either by cannula or vacuum transfer to the Schlenk flask. The Schlenk flask may be fitted with a reflux condenser, and the reaction mixture may be refluxed under nitrogen or static vacuum for 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., toluene, dichloromethane, dodecane, or a combination thereof).

Example 21

Synthesis of Tris(pentafluorophenyl)phosphine Oxide, $OP(C_6F_5)_3$

Bis(pentafluorophenyl)zinc and a phosphorus (V) trihalide oxide {e.g., phosphorus (V) trichloride oxide} may be added to a Schlenk flask along with a magnetic stir bar under nitrogen inside a glove box. The molar ratio of these two reagents should be maintained at a level of 3:2, respectively. The Schlenk flask may be sealed and attached to a Schlenk line, and then placed under nitrogen or vacuum. A sufficient quantity (enough to dissolve everything) of a suitable dry solvent (e.g., toluene, dichloromethane, dodecane, or a combination thereof) may be added either by cannula or vacuum transfer to the Schlenk flask. The Schlenk flask may be fitted with a reflux condenser, and the reaction mixture may be refluxed under nitrogen or static vacuum for 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by sublimation at a pressure of $10^{-2}$ Torr and 150° C. or by recrystallization from a suitable dry solvent (e.g., toluene, dichloromethane, dodecane, or a combination thereof).

Example 22

Synthesis of Lithium Hexakis(pentafluorophenyl) phosphate, $LiP(C_6F_5)_6$

Bis(pentafluorophenyl)zinc and a lithium phosphorus (VI) halide (i.e., lithium hexafluorophosphate) may be added to a Schlenk flask along with a magnetic stir bar under nitrogen inside a glove box. The molar ratio of these two reagents should be maintained at a level of 3:1, respectively. The Schlenk flask may be sealed and attached to a Schlenk line, then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser. The reaction mixture may be refluxed under nitrogen or static vacuum for 12 hours and then cooled to room temperature. Any zinc (II) dihalide that precipitates may be removed by replacing the condenser with a Schlenk frit/flask assembly and filtering the reaction mixture. The filtrate may be concentrated to a solid can by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof). Other Group 1 metal hexakis(pentafluorophenyl)phosphate compounds may be made by substitution of the desired Group 1 metal phosphorus (VI) halide (i.e., sodium hexafluorophosphate).

Example 23

Synthesis of Triphenylcarbenium Hexakis(pentafluorophenyl)phosphate, $(C_6H_5)_3CP(C_6F_5)_6$ Bis(pentafluorophenyl)zinc, a Group 1 metal halide phosphorus (VI) halide (i.e., lithium or sodium hexafluorophosphate), and a triphenylcarbenium halide (i.e., triphenylcarbenium chloride) may be added to a Schlenk flask along with a magnetic stir bar under nitrogen inside a glove box. The molar ratio of these three reagents should be maintained at a level of 3:1:1, respectively. The Schlenk flask may be sealed and attached to a Schlenk line and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser. The reaction mixture may be refluxed under nitrogen or static vacuum for 12 hours and then cooled to room temperature. Any Group 1 metal halide, or zinc (II) dihalide that precipitates may be removed by replacing the condenser with a Schlenk frit/flask assembly and filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof).

Example 24

Synthesis of Triphenylcarbenium Hexakis(pentafluorophenyl)phosphate, $(C_6H_5)_3CP(C_6F_5)_6$ Bis(pentafluorophenyl)zinc and a triphenylcarbenium phosphorus (VI) halide (i.e., triphenylcarbenium hexafluorophosphate) may be added to a Schlenk flask along with a magnetic stir bar under nitrogen inside a glove box. The molar ratio of these two reagents should be maintained at a level of 3:1, respectively. The Schlenk flask may be sealed and attached to a Schlenk line, and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser, and the reaction mixture may be refluxed under nitrogen or static vacuum for 12 hours and then cooled to room temperature. Any zinc (II) dihalide that precipitates may be removed by replacing the condenser with a Schlenk frit/flask assembly and filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof).

Example 25

Synthesis of Dimethylanilinium Hexakis(pentafluorophenyl)phosphate, $C_6H_5N[(CH_3)_2H]P(C_6F_5)_6$ A Group 1 metal hexakis(pentafluorophenyl)phophate (e.g., lithium hexakis(pentafluorophenyl)phosphate) and a dimethylanilinium halide (e.g., dimethylanilinium bromide) may be added to a Schlenk flask along with a magnetic stir bar under nitrogen inside a glove box. The molar ratio of these two reagents should be maintained at a level of 1:1, respectively. The Schlenk flask may be sealed and attached to a Schlenk line, and then placed under nitrogen or vacuum. A sufficient quantity (enough to dissolve everything) of a suitable dry solvent (e.g., acetonitrile, diethyl ether, toluene, dichloromethane, dodecane, or a combination thereof) may be added either by cannula or vacuum transfer to the Schlenk flask. The Schlenk flask may be fitted with a reflux condenser and the reaction mixture refluxed under nitrogen or static vacuum for 12 hours. It may then be cooled to room temperature. Any Group 1 metal halide that precipitates may be removed by replacing the condenser with a Schlenk frit/flask assembly and filtering the reaction mixture. The filtrate may be concentrated to a solid by removal of volatiles under reduced pressure. The crude material may be purified by recrystallization from a suitable dry solvent (e.g., acetonitrile, diethyl ether, toluene, dichloromethane, dodecane, or a combination thereof)

Example 26

Synthesis of Tris(pentafluorophenyl)antimony, $Sb(C_6F_5)_3$

Bis(pentafluorophenyl)zinc and an antimony (III) halide {i.e., antimony (III) chloride} may be added to a Schlenk flask along with a magnetic stir bar under nitrogen inside a glove box. The molar ratio of these two reagents is maintained at a level of 3:2, respectively. The Schlenk flask may be attached to a Schlenk line then placed under nitrogen or vacuum. A sufficient quantity (enough to dissolve everything) of a suitable dry solvent (i.e., toluene, dichloromethane, dodecane, or a combination thereof) may be added by either cannula or vacuum transfer to the Schlenk flask. The Schlenk flask may then be fitted with a reflux condenser and the reaction mixture may be refluxed under nitrogen or static vacuum for 12 hours and then cooled to room temperature. The condenser may then be replaced with a Schlenk frit/flask assembly and the reaction mixture then filtered. The filtrate may then be concentrated to a solid by removal of volatiles under reduced pressure. Unreacted bis(pentafluorophenyl) zinc may be removed via sublimation at a pressure of $10^{-2}$ Torr and 110° C. The unsublimed material may be purified by sublimation at a pressure of $10^{-2}$ Torr and 150° C. or by recrystallization from a suitable dry solvent (i.e., toluene, dichloromethane, dodecane, or a combination thereof).

Example 27

Synthesis of Pentakis(pentafluorophenyl)antimony, $Sb(C_6F_5)_5$

Bis(pentafluorophenyl)zinc and an antimony (V) halide {i.e., antimony (V) chloride} may be added to a Schlenk flask along with a magnetic stir bar under nitrogen inside a glove box. The molar ratio of these two reagents is maintained at a level of 5:2, respectively. The Schlenk flask may then be sealed and attached to a Schlenk line and placed under nitrogen or vacuum. A sufficient quantity (enough to dissolve everything) of a suitable dry solvent (i.e., toluene, dichloromethane, dodecane, or a combination thereof) may be added either by cannula or vacuum transfer to the Schlenk flask. The Schlenk flask may be fitted with a reflux condenser and the reaction mixture refluxed under nitrogen or static vacuum for 12 hours and then cooled to room temperature. The condenser may be replaced with a Schlenk frit/flask assembly and the reaction mixture filtered. The filtrate may be concentrated to a solid by removal of volatiles under reduced pressure. Unreacted bis(pentafluorophenyl)zinc may be removed via sublimation at a pressure of $10^{-2}$ Torr and 110° C. The unsublimed material may be purified by recrystallization from a suitable dry solvent (i.e., toluene, dichloromethane).

Example 28

Synthesis of Lithium Hexakis(pentafluorophenyl) antimonate, $LiSb(C_6F_5)_6$

Bis(pentafluorophenyl)zinc and a lithium antimony (VI) halide (i.e., lithium hexafluoroantimonate) may be added to a Schlenk flask along with a magnetic stir bar under nitrogen inside a glove box. The molar ratio of these two reagents is maintained at a level of 3:1, respectively. The Schlenk flask may be sealed and attached to a Schlenk line and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser and the reaction mixture refluxed under nitrogen or static vacuum for 12 hours and then cooled to room temperature. To remove any zinc (II) dihalide that precipitates the condenser may be replaced with a Schlenk frit/flask assembly and the reaction mixture filtered. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof). Other Group 1 metal hexakis(pentafluorophenyl)antimonate compounds may be made by substitution of the desired Group 1 metal antimony (VI) halide (i.e., sodium hexafluoroantimonate).

Example 29

Synthesis of Triphenylcarbenium Hexakis(pentafluorophenyl)antimonate, $(C_6H_5)_3CSb(C_6F_5)_6$ Bis(pentafluorophenyl)zinc, a Group 1 metal antimony (VI) halide (i.e., lithium or sodium hexafluoroantimonate), and a triphenylcarbenium halide (i.e., triphenylcarbenium chloride) may be added to a Schlenk flask along with a magnetic stir bar under nitrogen inside a glove box. The molar ratio of these three reagents is maintained at a level of 3:1:1, respectively. The Schlenk flask may be sealed and attached to a Schlenk line and then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser and the reaction mixture refluxed under nitrogen or static vacuum for 12 hours and then cooled to room temperature. Any Group 1 metal halide, or zinc (II) dihalide that precipitates may be removed by replacing the condenser with a Schlenk frit/flask assembly and then filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof).

Example 30

Synthesis of Triphenylcarbenium Hexakis(pentafluorophenyl)antimonate, $(C_6H_5)_3CSb(C_6F_5)_6$ Bis(pentafluorophenyl)zinc and a triphenylcarbenium antimony (VI) halide (i.e., triphenylcarbenium hexachloroantimonate) may be added to a Schlenk flask along with a magnetic stir bar under nitrogen inside a glove box. The molar ratio of these two reagents is maintained at a level of 3:1, respectively. The Schlenk flask may be attached to a Schlenk line then placed under nitrogen or vacuum. A sufficient quantity (enough to dissolve everything) of a suitable dry solvent (i.e., acetonitrile, diethyl ether, toluene, dichloromethane, dodecane, or a combination thereof) may be added either by cannula or vacuum transfer to the Schlenk flask. The Schlenk flask may be fitted with a reflux condenser and the reaction mixture refluxed under nitrogen or static vacuum for 12 hours and then cooled to room temperature. Any zinc (II) dihalide that precipitates may be removed by replacing the condenser with a Schlenk frit/flask assembly and filtering the reaction mixture. The filtrate may be concentrated to a solid by removal of volatiles under reduced pressure. Any unreacted bis(pentafluorophenyl)zinc may be removed via sublimation at a pressure of $10^{-2}$ Torr and 110° C. The unsublimed material may be purified by recrystallization from a suitable dry solvent (i.e., acetonitrile, diethyl ether, toluene, dichloromethane, dodecane, or a combination thereof).

Example 31

Synthesis of Dimethylanilinium Hexakis(pentafluorophenyl)antimonate, $C_6H_5N[(CH_3)_2H]Sb(C_6F_5)_6$ A Group 1 metal hexakis(pentafluorophenyl)antimonate (e.g., lithium hexakis(pentafluorophenyl)antimonate) and a dimethylanilinium halide (e.g., dimethylanilinium bromide) may be added to a Schlenk flask along with a magnetic stir bar under nitrogen inside a glove box. The molar ratio of these two reagents is maintained at a level of 1:1, respectively. The Schlenk flask may be sealed and attached to a Schlenk line then placed under nitrogen or vacuum. A sufficient quantity (enough to dissolve everything) of a suitable dry solvent (e.g., acetonitrile, diethyl ether, toluene, dichloromethane, dodecane, or a combination thereof) may be added either by cannula or vacuum transfer to the Schlenk flask. The Schlenk flask may be fitted with a reflux condenser and the reaction mixture refluxed under nitrogen or static vacuum for 12 hours and then cooled to room temperature. Any Group 1 metal halide that precipitates may be removed by replacing the condenser with a Schlenk frit/flask assembly and then filtering the reaction mixture. The filtrate may be concentrated to a solid by removal of volatiles under reduced pressure. The crude material may be purified by recrystallization from a suitable dry solvent (e.g., acetonitrile, diethyl ether, toluene, dichloromethane, dodecane, or a combination thereof).

Example 33

Synthesis of Tetra(pentafluorophenyl) Diboron, $B_2(C_6F_5)_4$

Bis(pentafluorophenyl)zinc (in toluene) may be added to a Schlenk flask containing a magnetic stir bar and a determined quantity of diboron tetrahalide (e.g. diboron tetrabromide) under nitrogen so that the molar ratio of diboron tetrabromide to bis(pentafluorophenyl)zinc is 1:2. The reaction mixture may be stirred for 12 hours and then the Schlenk flask may be fitted with a Schlenk frit/flask assembly. Any zinc (II) dihalide that precipitates may be removed by replacing the condenser with a Schlenk frit/flask assembly and filtering the reaction mixture. The filtrate may be concentrated to a solid by removal of volatiles under reduced pressure. The crude product may be recrystallized from a suitable dry solvent (e.g. toluene, dichloromethane).

Example 31

Synthesis of 1,2-bis[di(perfluorophenyl)boron]-3,4,5,6-tetrafluorobenzene, $1,2-C_6F_4[B(C_6F_5)_2]_2$ 1,2-bis(copper)-3,4,5,6-tetrafluorobenzene may be added to a Schlenk flask along with a magnetic stir bar under nitrogen inside a glove box. The Schlenk flask may be sealed and attached to a Schlenk line then placed under nitrogen or vacuum. A sufficient quantity of a boron (III) halide {e.g., boron (III) bromide} may be dissolved in a suitable solvent (e.g. toluene) and added either by cannula or vacuum transfer to the Schlenk flask {so that the molar ratio of 1,2-bis(copper)-3,4,5,6-tetrafluorobenzene to boron (III) halide is 1:2, respectively}. The Schlenk flask may be fitted with a reflux condenser and to >100° C. under nitrogen or static vacuum for 12 hours and then cooled to room temperature. Bis(pentafluorophenyl)zinc as a solution in the same solvent as that previously used may be added either by cannula or syringe. The molar ratio of this reagent with respect to the boron (III) halide should be $\geqq 1:1$, respectively. The reaction may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)boron may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 32

Synthesis of 1,2-bis[di(perfluorophenyl)gallium]-3,4,5,6-tetrafluoro-benzene, $1,2-C_6F_4[Ga(C_6F_5)_2]_2$ Tris(perfluoro-o-phenylenemercury) and a gallium (III) halide {i.e., gallium (III) chloride} may be added to a Schlenk flask along with a magnetic stir bar under nitrogen inside a glove box. The molar ratio of these two reagents is maintained at a level of $\leqq 1:6$, respectively. The Schlenk flask may be attached to a Schlenk line then placed either under nitrogen or vacuum. A sufficient quantity {enough to dissolve the gallium (III) halide} of a suitable dry solvent (i.e., toluene, dichloromethane, dodecane, or a combination thereof) may be added by cannula to the Schlenk flask. The Schlenk flask may be fitted with a reflux condenser and the reaction mixture refluxed under nitrogen or static vacuum for 12 hours and then cooled to room temperature. Bis(pentafluorophenyl)zinc as a solution in the same solvent as that previously used may be added either by cannula or syringe. The molar ratio of this reagent with respect to the gallium (III) halide should be $\geqq 1:1$, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)gallium may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 33

Synthesis of 1,2-bis[di(perfluorophenyl)gallium]-3,4,5,6-tetrafluoro-benzene, $1,2\text{-}C_6F_4[Ga(C_6F_5)_2]_2$ 1,2-bis(copper)-3,4,5,6-tetrafluorobenzene may be added to a Schlenk flask along with a magnetic stir bar under nitrogen inside a glove box. The Schlenk flask may be attached to a Schlenk line then placed under nitrogen or vacuum. A sufficient quantity of a gallium (III) halide {e.g., gallium (III) bromide} dissolved in a suitable solvent (e.g. toluene) may be added by cannula to the Schlenk flask {so that the molar ratio of 1,2-bis(copper)-3,4,5,6-tetrafluorobenzene to gallium (III) halide is 1:2, respectively}. The Schlenk flask may be fitted with a reflux condenser and the reaction mixture heated to >100° C. under nitrogen or static vacuum for 12 hours then cooled to room temperature. Bis(pentafluorophenyl)zinc as a solution in the same solvent as that previously used may be added either by cannula or syringe. The molar ratio of this reagent with respect to the gallium (III) halide should be $\geq 1:1$, respectively. The reaction mixture may be reheated to reflux for another 12 hours and then cooled to room temperature. The condenser may then be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)gallium may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 34

Synthesis of 1,2-bis[di(perfluorophenyl)indium]-3,4,5,6-tetrafluoro-benzene, $1,2\text{-}C_6F_4[In(C_6F_5)_2]_2$ Tris(perfluoro-o-phenylenemercury) and an indium (III) halide {i.e., indium (III) chloride} may be added to a Schlenk flask along with a magnetic stir bar under nitrogen inside a glove box. The molar ratio of these two reagents is maintained at a level of $\leq 1:6$, respectively. The Schlenk flask may be sealed and attached to a Schlenk line then placed either under nitrogen or vacuum. A sufficient quantity {enough to dissolve the indium (III) halide} of a suitable dry solvent (i.e., toluene, dichloromethane, dodecane, or a combination thereof) may be added by cannula to the Schlenk flask. The Schlenk flask may be fitted with a reflux condenser and the reaction mixture refluxed under nitrogen or static vacuum for 12 hours and then cooled to room temperature. Bis(pentafluorophenyl)zinc as a solution in the same solvent as that previously used may be added either by cannula or syringe. The molar ratio of this reagent with respect to the indium (III) halide should be $\geq 1:1$, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)indium may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 35

Synthesis of 1,2-bis[di(perfluorophenyl)indium]-3,4,5,6-tetrafluoro-benzene, $1,2\text{-}C_6F_4[In(C_6F_5)_2]_2$ 1,2-bis(copper)-3,4,5,6-tetrafluorobenzene may be added to a Schlenk flask along with a magnetic stir bar under nitrogen inside a glove box. The Schlenk flask may be attached to a Schlenk line then placed under nitrogen or vacuum. A sufficient quantity of a indium (III) halide {e.g., indium (III) bromide} dissolved in a suitable solvent (e.g. toluene) may be added by cannula to the Schlenk flask {so that the molar ratio of 1,2-bis(copper)-3,4,5,6-tetrafluorobenzene to indium (III) halide is 1:2, respectively}. The Schlenk flask may be fitted with a reflux condenser and the reaction mixture heated to >100° C. under nitrogen or static vacuum for 12 hours then cooled to room temperature. Bis(pentafluorophenyl)zinc as a solution in the same solvent as that previously used may be added either by cannula or syringe. The molar ratio of this reagent with respect to the indium (III) halide should be $\geq 1:1$, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)indium may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 36

Synthesis of 1,2-bis[di(perfluorophenyl)thallium]-3,4,5,6-tetrafluoro-benzene, $1,2\text{-}C_6F_4[Tl(C_6F_5)_2]_2$ Tris(perfluoro-o-phenylenemercury) and an thallium (III) halide {e.g., thallium (III) chloride} may be added to a Schlenk flask along with a magnetic stir bar under nitrogen inside a glove box. The molar ratio of these two reagents is maintained at a level of $\leq 1:6$, respectively. The Schlenk flask may be sealed and attached to a Schlenk line then placed either under nitrogen or vacuum. A sufficient quantity {enough to dissolve the thallium (III) halide} of a suitable dry solvent (e.g., toluene, dichloromethane, dodecane, or a combination thereof) may be added either by cannula or vacuum transfer to the Schlenk flask. The Schlenk flask may be fitted with a reflux condenser and the reaction mixture refluxed under nitrogen or static vacuum for 12 hours and then cooled to room temperature. Bis(pentafluorophenyl)zinc as a solution in the same solvent as that previously used may be added either by cannula or syringe. The molar ratio of this reagent with respect to the thallium (III) halide should be $\geq 1:1$, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)thallium may be removed via sublimation at a pressure of $10^{-2}$ Torr and 110° C. and 150° C. respectively. The unsublimed material may be purified by recrystallization from a suitable dry solvent (e.g., toluene, dichloromethane, dodecane, or a combination thereof).

Example 37

Synthesis of 1,2-bis[di(perfluorophenyl)thallium]-3,4,5,6-tetrafluoro-benzene, 1,2-$C_6F_4$[Tl$(C_6F_5)_2]_2$ 1,2-bis(copper)-3,4,5,6-tetrafluorobenzene may be added to a Schlenk flask along with a magnetic stir bar under nitrogen inside a glove box. The Schlenk flask may be sealed and attached to a Schlenk line then placed under nitrogen or vacuum. A sufficient quantity of a thallium (III) halide {e.g., thallium (III) bromide} dissolved in a suitable solvent (e.g. toluene) may be added by cannula to the Schlenk flask {so that the molar ratio of 1,2-bis(copper)-3,4,5,6-tetrafluorobenzene to thallium (III) halide is 1:2, respectively}. The Schlenk flask may be fitted with a reflux condenser and the reaction mixture heated to >100° C. under nitrogen or static vacuum for 12 hours then cooled to room temperature. Bis(pentafluorophenyl)zinc as a solution in the same solvent as that previously used may be added either by cannula or syringe. The molar ratio of this reagent with respect to the thallium (III) halide should be $\geq$1:1, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)thallium may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof)

Example 38

Synthesis of 1,2-bis[di(perfluorophenyl)phosphorus]-3,4,5,6-tetrafluoro-benzene, 1,2-$C_6F_4$[P$(C_6F_5)_2]_2$ Tris(perfluoro-o-phenylenemercury) and a phosphorus (III) halide (i.e., phosphorus (III) chloride)} may be added to a Schlenk flask along with a magnetic stir bar under nitrogen inside a glove box. The molar ratio of these two reagents is maintained at a level of $\leq$1:6, respectively. The Schlenk flask may be attached to a Schlenk line and then placed either under nitrogen or vacuum. A sufficient quantity {enough to dissolve the phosphorus (III) halide} of a suitable dry solvent (i.e., toluene, dichloromethane, dodecane, or a combination thereof) may be added either by cannula or vacuum transfer to the Schlenk flask. The Schlenk flask may be fitted with a reflux condenser and the reaction mixture refluxed under nitrogen or static vacuum for 12 hours and then cooled to room temperature. Bis(pentafluorophenyl)zinc as a solution in the same solvent as that previously used may be added either by cannula or syringe. The molar ratio of this reagent with respect to the phosphorus (III) halide should be $\geq$1:1, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)phosphorus may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 39

Synthesis of 1,2-bis[di(perfluorophenyl)phosphorus]-3,4,5,6-tetrafluoro-benzene, 1,2-$C_6F_4$[P$(C_6F_5)_2]_2$ 1,2-bis(copper)-3,4,5,6-tetrafluorobenzene may be added to a Schlenk flask along with a magnetic stir bar under nitrogen inside a glove box. The Schlenk flask may be attached to a Schlenk line then placed under nitrogen or vacuum. A sufficient quantity of a phosphorus (III) halide {e.g., phosphorus (III) bromide} dissolved in a suitable solvent (e.g. toluene) may be added by cannula to the Schlenk flask {so that the molar ratio of 1,2-bis(copper)-3,4,5,6-tetrafluorobenzene to phosphorus (III) halide is 1:2, respectively}. The Schlenk flask may be fitted with a reflux condenser and the reaction mixture heated to >100° C. under nitrogen or static vacuum for 12 hours then cooled to room temperature. Bis(pentafluorophenyl)zinc as a solution in the same solvent as that previously used may be added either by cannula or syringe. The molar ratio of this reagent with respect to the phosphorus (III) halide should be $\geq$1:1, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)phosphorus may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof)

Example 40

Synthesis of 1,2-bis[di(perfluorophenyl)arsenic]-3,4,5,6-tetrafluoro-benzene, 1,2-$C_6F_4$[As$(C_6F_5)_2]_2$ Tris(perfluoro-o-phenylenemercury) and an arsenic (III) halide {i.e., arsenic (III) chloride}} may be added to a Schlenk flask along with a magnetic stir bar under nitrogen inside a glove box. The molar ratio of these two reagents is maintained at a level of $\leq$1:6, respectively. The Schlenk flask may be sealed and attached to a Schlenk line then placed either under nitrogen or vacuum. A sufficient quantity {enough to dissolve the arsenic (III) halide} of a suitable dry solvent (i.e., toluene, dichloromethane, dodecane, or a combination thereof) may be added by cannula to the Schlenk flask. The Schlenk flask may be fitted with a reflux condenser and the reaction mixture refluxed under nitrogen or static vacuum for 12 hours and then cooled to room temperature. Bis(pentafluorophenyl)zinc as a solution in the same solvent as that previously used may be added either by cannula or syringe. The molar ratio of this reagent with respect to the arsenic (III) halide should be ≧1:1, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)arsenic may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 41

Synthesis of 1,2-bis[di(perfluorophenyl)arsenic]-3,4,5,6-tetrafluoro-benzene, 1,2-$C_6F_4[As(C_6F_5)_2]_2$ 1,2-bis(copper)-3,4,5,6-tetrafluorobenzene may be added to a Schlenk flask along with a magnetic stir bar under nitrogen inside a glove box. The Schlenk flask may be sealed and attached to a Schlenk line and then placed under nitrogen or vacuum. A sufficient quantity of a arsenic (III) halide {e.g., arsenic (III) bromide} dissolved in a suitable solvent (e.g. toluene) may be added by cannula to the Schlenk flask {so that the molar ratio of 1,2-bis(copper)-3,4,5,6-tetrafluorobenzene to arsenic (III) halide is 1:2, respectively}. The Schlenk flask may be fitted with a reflux condenser and the reaction mixture heated to >100° C. under nitrogen or static vacuum for 12 hours then cooled to room temperature. Bis(pentafluorophenyl)zinc as a solution in the same solvent as that previously used may be added either by cannula or syringe. The molar ratio of this reagent with respect to the arsenic (III) halide should be ≧1:1, respectively. The reaction mixture may be reheated to reflux for another 12 hours and then cool to room temperature. The condenser may be replaced with a Schlenk frit/flask assembly and filter the reaction mixture. The filtrate may be concentrated to a solid by removal of volatiles under reduced pressure. Any unreacted bis(pentafluorophenyl)zinc or byproduct tris(pentafluorophenyl)arsenic may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 42

Synthesis of 1,2-bis[di(perfluorophenyl)antimony]-3,4,5,6-tetrafluorobenzene, 1,2-$C_6F_4[Sb(C_6F_5)_2]_2$ Tris(perfluoro-o-phenylenemercury) and an antimony (III) halide {i.e., antimony (III) chloride} may be added to a Schlenk flask along with a magnetic stir bar under nitrogen inside a glove box. The molar ratio of these two reagents is maintained at a level of ≦1:6, respectively. The Schlenk flask may be sealed and attached to a Schlenk line then placed either under nitrogen or vacuum. A sufficient quantity {enough to dissolve the antimony (III) halide} of a suitable dry solvent (i.e., toluene, dichloromethane, dodecane, or a combination thereof) may be added either by cannula or vacuum transfer to the Schlenk flask. The Schlenk flask may be fitted with a reflux condenser and the reaction mixture refluxed under nitrogen or static vacuum for 12 hours and then cooled to room temperature. Bis(pentafluorophenyl)zinc as a solution in the same solvent as that previously used may be added either by cannula or syringe. The molar ratio of this reagent with respect to the antimony (III) halide should be ≧1:1, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)antimony may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 43

Synthesis of 1,2-bis[di(perfluorophenyl)antimony]-3,4,5,6-tetrafluoro-benzene, 1,2-$C_6F_4[Sb(C_6F_5)_2]_2$ 1,2-bis(copper)-3,4,5,6-tetrafluorobenzene may be added to a Schlenk flask along with a magnetic stir bar under nitrogen inside a glove box. The Schlenk flask may be sealed and attached to a Schlenk line then placed under nitrogen or vacuum. A sufficient quantity of a antimony (III) halide {e.g., antimony (III) bromide} dissolved in a suitable solvent (e.g. toluene) may be added by cannula the Schlenk flask {so that the molar ratio of 1,2-bis(copper)-3,4,5,6-tetrafluorobenzene to antimony (III) halide is 1:2, respectively}. The Schlenk flask may be fitted with a reflux condenser and the reaction mixture heated to >100° C. under nitrogen or static vacuum for 12 hours then cooled to room temperature. Bis(pentafluorophenyl)zinc may be added as a solution in the same solvent as that previously used either by cannula or syringe. The molar ratio of this reagent with respect to the antimony (III) halide should be ≧1:1, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)antimony may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof)

Example 44

Synthesis of 1,2-bis[di(perfluorophenyl)bismuth]-3,4,5,6-tetrafluoro-benzene, 1,2-$C_6F_4[Bi(C_6F_5)_2]_2$ Tris(perfluoro-o-phenylenemercury) and a bismuth (III) halide {i.e., bismuth (III) chloride} may be added to a Schlenk flask along with a magnetic stir bar under nitrogen inside a glove box. The molar ratio of these two reagents is maintained at a level of ≦1:6, respectively. The Schlenk flask may be sealed and attached to a Schlenk line then placed either under nitrogen or vacuum. A sufficient quantity {enough to dissolve the bismuth (III) halide} of a suitable dry solvent (i.e., toluene, dichloromethane, dodecane, or a combination thereof) may be added either by cannula or vacuum transfer to the Schlenk flask. The Schlenk flask may be fitted with a reflux condenser and the reaction mixture heated to reflux under nitrogen or static vacuum for 12 hours and then cooled to room temperature. Bis(pentafluorophenyl)zinc as a solution in the same solvent as that previously used may be added either by cannula or syringe. The molar ratio of this reagent with respect to the bismuth (III) halide should be $\geqq 1:1$, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)bismuth may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 45

Synthesis of 1,2-bis[di(perfluorophenyl)bismuth]-3, 4,5,6-tetrafluoro-benzene, 1,2-$C_6F_4[Bi(C_6F_5)_2]_2$ 1,2-bis(copper)-3,4,5,6-tetrafluorobenzene may be added to a Schlenk flask along with a magnetic stir bar under nitrogen inside a glove box. The Schlenk flask may be sealed and attached to a Schlenk line and then placed under nitrogen or vacuum. A sufficient quantity of a bismuth (III) halide {e.g., bismuth (III) bromide} dissolved in a suitable solvent (e.g. toluene) may be added by cannula to the Schlenk flask {so that the molar ratio of 1,2-bis(copper)-3,4,5,6-tetrafluorobenzene to bismuth (III) halide is 1:2, respectively}. The Schlenk flask may be fitted with a reflux condenser and the reaction mixture heated to >100° C. under nitrogen or static vacuum for 12 hours then cooled to room temperature. Bis (pentafluorophenyl)zinc as a solution in the same solvent as that previously used may be added either by cannula or syringe. The molar ratio of this reagent with respect to the bismuth (III) halide should be $\geqq 1:1$, respectively. The reaction mixture may be reheated to reflux for another 12 hours and then cooled to room temperature. The condenser may be replaced with a Schlenk frit/flask assembly and the reaction mixture filtered. The filtrate may be concentrated to a solid by removal of volatiles under reduced pressure. Any unreacted bis(pentafluorophenyl)zinc or byproduct tris(pentafluorophenyl)bismuth may be removed via sublimation at a pressure of $10^{-2}$ Torr and 110° C. and 150° C. respectively. The unsublimed material may be purified by recrystallization from a suitable dry solvent (i.e., toluene, dichloromethane, dodecane, or a combination thereof).

Example 46

Polymerization of Isobutene with Tetra(pentafluorophenyl) Diboron, $B_2(C_6F_5)_4$ A 250-mL, round-bottom, 24/40, single-neck flask may be charged with 11.4 g (18.0 mL) of pre-dried hexanes, 0.82 g (1.00 mL) of trioctylaluminum, and a magnetic stir bar inside a glove box. The flask may be fitted with a 24/40 vacuum adapter equipped with a Teflon vacuum stopcock and connected to a vacuum line. This may then be degassed using three freeze-pump-thaw cycles and subsequently charged with 5.50 mL monomer via vacuum transfer. This solution may be stirred at −78° C. for 30 minutes and then both monomer and solvent may be transferred under vacuum into a second, two-neck, round-bottom flask attached to the vacuum line through another 24/40 vacuum adapter and equipped with a septum inlet. The contents of this flask may be warmed to −78° C. and stirred for 15 min under $N_2$. 1.00 mL of a stock solution of $B_2(C_6F_5)_4$ ($5.00\times10^{-2}$ M in toluene) may then be injected into the flask. After polymerization is completed the reaction may be quenched with methanol and the polymer isolated by removal of solvent by evaporation.

Example 47

Polymerization of Ethylene using Tetra(pentafluorophenyl) Diboron, $B_2(C_6F_5)_4$ A glass pressure reactor may be loaded with $1.26\times10^{-2}$ g ($5.00\times10^{-5}$ mol) bis(cyclopentadienyl)dimethylzirconium, a magnetic stir bar, and 25.00 mL of dry toluene inside of a glove box under nitrogen. The reactor may be sealed and connected to an ethylene tank. The reactor may then be placed under a pressure of 30 psi ethylene the system allowed to equilibrate for 30 minutes with stirring. The reactor may be closed off from the ethylene supply and next 1.00 mL of a stock solution of $B_2(C_6F_5)_4$ ($5.00\times10^{-2}$ M in toluene) may be injected. The polymerization may then be allowed to run to completion and then the reactor vented. The polymer may be precipitated in methanol and the methanol decanted to obtain the polymer.

Example 48

Polymerization of Isobutene with 1,2-bis[di(perfluorophenyl)gallium]-3,4,5,6-tetrafluorobenzene, 1,2-$C_6F_4[Ga(C_6F_5)_2]_2$ A 250-mL, round-bottom, 24/40, single-neck flask may be charged with 11.4 g (18.0 mL) of pre-dried hexanes, 0.82 g (1.00 mL) of trioctylaluminum, and a magnetic stir bar inside a glove box. The flask may be fitted with a 24/40 vacuum adapter equipped with a Teflon vacuum stopcock and connected to a vacuum line. This may be degassed using three freeze-pump-thaw cycles and subsequently charged with 5.50 mL monomer via vacuum transfer. This solution may be stirred at −78° C. for 30 minutes and then both monomer and solvent may be transferred under vacuum into a second, two-neck, round-bottom flask attached to the vacuum line through another 24/40 vacuum adapter and equipped with a septum inlet. The contents of this flask may be warmed to −78° C. and stirred for 15 min under $N_2$. 1.00 mL of a stock solution of 1,2-$C_6F_4[Ga(C_6F_5)_2]_2$ ($5.00\times10^{-2}$ M in toluene) may then be injected into the flask. After polymerization is completed the reaction may be quenched with methanol and the polymer isolated by removal of solvent by evaporation.

Example 49

Polymerization of Ethylene using 1,2-bis[di(perfluorophenyl)gallium]-3,4,5,6-tetrafluorobenzene, 1,2-$C_6F_4[Ga(C_6F_5)_2]_2$ A glass pressure reactor may be loaded with $1.26\times10^{-2}$ g ($5.00\times10^{-5}$ mol) bis(cyclopentadienyl)dimethylzirconium, a magnetic stir bar, and 25.00 mL of dry toluene inside of a glove box under nitrogen. The reactor may be sealed and connected to an ethylene tank. The reactor may then be placed under a pressure of 30 psi ethylene the system allowed to equilibrate for 30 minutes with stirring. The reactor may be closed off from the ethylene supply and 1.00 mL of a stock solution of 1,2-$C_6F_4[Ga(C_6F_5)_2]_2$ ($5.00\times10^{-2}$ M in toluene) may then be injected. The polymerization may then be allowed to run to completion and then the reactor vented. The polymer may then be precipitated in methanol and the methanol decanted to obtain the polymer.

Example 50

Polymerization of Ethylene using Triphenylcarbenium Hexakis(penta-fluorophenyl)phosphate, $(C_6H_5)_3CP(C_6F_5)_6$ A glass pressure reactor may be charged with $1.26 \times 10^{-2}$ g ($5.00 \times 10^{-5}$ mol) bis(cyclopenta dienyl)dimethylzirconium, a magnetic stir bar, and 25.00 mL of dry toluene inside of a glove box under nitrogen. The reactor may be sealed and connected to an ethylene tank. The reactor may then be placed under a pressure of 30 psi ethylene the system allowed to equilibrate for 30 minutes with stirring. The reactor may be closed off from the ethylene supply and 1.00 mL of a stock solution of $(C_6H_5)_3CP(C_6F_5)_6$ ($5.00 \times 10^{-2}$ M in toluene) may then be inject. The polymerization may then be allowed to run to completion and then the reactor vented. The polymer may then be precipitated in methanol and the methanol decanted to obtain the polymer.

When ranges are used herein for physical properties, such as molecular weight, or chemical properties, such as chemical formulae, all combinations, and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A process, comprising the steps of:
    a. contacting, in a bulk melt state:
        i. pentafluorobenzoic acid with a Group 11 or 12 metal oxide, a Group 11 or 12 metal hydroxide, a Group 11 or 12 metal carbonate, or a Group 11 or 12 metal acetate under neutralizing conditions; or
        ii. a Group 1 or 2 metal salt of pentafluorobenzoic acid with a Group 11 or 12 metal halide;
        to form a Group 11 or 12 pentafluorobenzoate;
    b. removing volatiles; and
    c. decarboxylating said Group 11 or 12 pentafluorobenzoate to form a (pentafluorophenyl) Group 11 or 12 metal compound.

2. The process according to claim 1,
    wherein said (pentafluorophenyl) Group 11 or 12 metal compound comprises a metal selected from the group consisting of copper (Cu), silver (Ag), zinc (Zn), cadmium (Cd), and mercury (Hg).

3. The process according to claim 1,
    wherein said (pentafluorophenyl) Group 11 or 12 metal compound comprises a metal selected from the group consisting of copper (Cu) and zinc (Zn).

4. The process according to claim 1,
    wherein said (pentafluorophenyl) Group 11 or 12 metal compound is:
    bis(pentafluorophenyl)zinc $[Zn(C_6F_5)_2]$;
    bis(pentafluorophenyl)copper $[Cu(C_6F_5)_2]$; or
    pentafluorophenylcopper tetramer $[(CuC_6F_5)_4]$.

5. The process according to claim 1,
    wherein said Group 1 or 2 metal salt of pentafluorobenzoic acid comprises a metal selected from the group consisting of lithium (Li), sodium (Na), potassium (K), magnesium (Mg), and calcium (Ca).

6. The process according to claim 1,
    wherein said step a is conducted in the substantial absence of solvent or diluent.

7. The process according to claim 1, further comprising the step of:
    d. contacting said (pentafluorophenyl) Group 11 or 12 metal compound with a Group 13 or 15 metal halide to form a (pentafluorophenyl) Group 13 or 15 metal compound.

8. The process according to claim 7,
    wherein said (pentafluorophenyl) Group 13 or 15 metal compound comprises a metal selected from the group consisting of boron (B), aluminum (Al), gallium (Ga), indium (In), nitrogen (N), phosphorus (P), antimony (Sb), and bismuth (Bi).

9. The process according to claim 7,
    wherein said (pentafluorophenyl) Group 13 or 15 metal compound is:
    tris(pentafluorophenyl)boron;
    lithium tetrakis(pentafluorophenyl)borate;
    sodium tetrakis(pentafluorophenyl)borate;
    potassium tetrakis(pentafluorophenyl)borate;
    triphenylcarbenium tetrakis(pentafluorophenyl)borate;
    tris(pentafluorophenyl)aluminum;
    lithium tetrakis(pentafluorophenyl)aluminate;
    sodium tetrakis(pentafluorophenyl)aluminate;
    potassium tetrakis(pentafluorophenyl)aluminate;
    triphenylcarbenium tetrakis(pentafluorophenyl)aluminate;
    tris(pentafluorophenyl)gallium;
    lithium tetrakis(pentafluorophenyl)gallate;
    sodium tetrakis(pentafluorophenyl)gallate;
    potassium tetrakis(pentafluorophenyl)gallate;
    triphenylcarbenium tetrakis(pentafluorophenyl)gallate;
    tris(pentafluorophenyl)indium;
    tris(pentafluorophenyl)amine;
    tris(pentafluorophenyl)phosphorus;
    pentakis(pentafluorophenyl)phosphorus;
    lithium hexakis(pentafluorophenyl)phosphate;
    sodium hexakis(pentafluorophenyl)phosphate;
    potassium hexakis(pentafluorophenyl)phosphate;
    triphenylcarbenium hexakis(pentafluorophenyl)phosphate;
    tris(pentafluorophenyl)arsenic;
    pentakis(pentafluorophenyl)arsenic;
    lithium hexakis(pentafluorophenyl)arsenate;
    sodium hexakis(pentafluorophenyl)arsenate;
    potassium hexakis(pentafluorophenyl)arsenate;
    triphenylcarbenium hexakis(pentafluorophenyl)arsenate;
    tris(pentafluorophenyl)antimony;
    pentakis(pentafluorophenyl)antimony;
    lithium hexakis(pentafluorophenyl)antimonate;
    sodium hexakis(pentafluorophenyl)antimonate;
    potassium hexakis(pentafluorophenyl)antimonate;
    triphenylcarbenium hexakis(pentafluorophenyl)antimonate;
    tris(pentafluorophenyl)bismuth;
    pentakis(pentafluorophenyl)bismuth;
    lithium hexakis(pentafluorophenyl)bismate;
    sodium hexakis(pentafluorophenyl)bismate;
    potassium hexakis(pentafluorophenyl)bismate;
    triphenylcarbenium hexakis(pentafluorophenyl)bismate;
    1,2-bis[di(perfluorophenyl)gallium]-3,4,5,6-tetrafluorobenzene;
    1,2-bis[di(perfluorophenyl)indium]-3,4,5,6-tetrafluorobenzene;

1,2-bis[di(perfluorophenyl)amino]-3,4,5,6-tetrafluorobenzene;
1,2-bis[di(perfluorophenyl)phosphorus]-3,4,5,6-tetrafluorobenzene;
1,2-bis[di(perfluorophenyl)bismuth]-3,4,5,6-tetrafluorobenzene;
1,2-bis[di(perfluorophenyl)arsenic]-3,4,5,6-tetrafluorobenzene; or
1,2-bis[di(perfluorophenyl)antimony]-3,4,5,6-tetrafluorobenzene.

10. The process according to claim 7, wherein said step d is carried out in a bulk melt state.

11. The process according to claim 2, further comprising the step of:
e. recovering said (pentafluorophenyl) Group 13 or 15 metal compound.

12. The process according to claim 11, wherein step e is effected by sublimation of said (pentafluorophenyl) Group 13 or 15 metal compound.

13. The process according to claim 11, wherein step e is effected by:
solubilizing said (pentafluorophenyl) Group 13 or 15 metal compound in at least one solvent that does not form a complex with Lewis acids to form a solution;
filtering or decanting said solution; and
optionally, evaporating said solvent to recover said purified (pentafluorophenyl) Group 13 or 15 metal compound.

14. A compound of the formula:

$$R_2Y\text{—}R'\text{—}YR_2$$

wherein:
Y is Ga, In, N, P, As, Sb, or Bi;
each R is independently selected from the group consisting of a perfluorophenyl; 3,5-bis(trifluoromethyl)phenyl; 1-perfluoronapthyl; 2-perfluoronaphthyl; 2-perfluorobiphenyl; 3-perfluorobiphenyl; 4-perfluorobiphenyl; and p-R''$_3$Si-2,3,5,6-tetra-fluorophenyl;
R' is 1,2-perfluorophenylenyl; 1,2-perfluoronaphthalenyl; 2,3-perfluoronapthalenyl; 1,8-perfluoronaphthalenyl; 1,2-perfluoroanthracenyl; 2,3-perfluoroanthracenyl; 1,9-perfluoroanthracenyl; 1,2-perfluorophenanthrenyl; 2,3-perfluorophenanthrenyl; 1,10-perfluorophenanthrenyl; 9,10-perfluorophenanthrenyl; 2,2'-perfluorobiphenylenyl; 2,2'-perfluoro-1,1'-binaphthalenyl; 3,3'-perfluoro-2,2'-binaphthalenyl;
or 1,1'-ferrocenyl; and
R' is a $C_1$-$C_{10}$ alkyl, wherein the compound is selected from the group consisting of:
1,2-bis[di(perfluorophenyl)gallium]-3,4,5,6-tetrafluorobenzene;
1,2-bis[di(perfluorophenyl)indium]-3,4,5,6-tetrafluorobenzene;
1,2-bis[di(perfluorophenyl)amino]-3,4,5,6-tetrafluorobenzene;
1,2-bis[di(perfluorophenyl)phosphorus]-3,4,5,6-tetrafluorobenzene;
1,2-bis[di(perfluorophenyl)arsenic]-3,4,5,6-tetrafluorobenzene;
1,2-bis[di(perfluorophenyl)antimony]-3,4,5,6-tetrafluorobenzene; and
1,2-bis[di(perfluorophenyl)bismuth]-3,4,5,6-tetrafluorobenzene.

15. A compound of the formula $$R_2Y\text{—}YR_2$$

wherein Y is B; and
each R is independently selected from the group consisting of a perfluorophenyl; 3,5-bis(trifluoromethyl)phenyl; 1-perfluoronaphthyl; 2-perfluoronaphthyl; 2-perfluorobiphenyl; 3-perfluorobiphenyl; 4-perfluorobiphenyl; and p-($C_1$-$C_{10}$ alkyl)$_3$Si-2,3,5,6-tetra-fluorophenyl.

16. The compound of claim 15, wherein the compound is a catalyst activator, and wherein said catayst activator may he reacted with at least one monomer and at least one metallocene catalyst to form a polymer.

17. The compound of claim 15, wherein the compound is a co-initiator that, together with an initiator that is a proton source or a carbocation synthetic equivalent, reacts at least one monomer to form a polymer.

* * * * *